United States Patent
Lee et al.

(10) Patent No.: US 9,522,240 B2
(45) Date of Patent: Dec. 20, 2016

(54) VISUALIZATION APPARATUS FOR VEIN

(71) Applicant: KOREA INSTITUTE OF SCIENCE AND TECHNOLOGY, Seoul (KR)

(72) Inventors: Deukhee Lee, Seoul (KR); Se Hyung Park, Seoul (KR); Sung Hwan Lim, Seoul (KR); Sangjun Lee, Seoul (KR)

(73) Assignee: Korea Institute Of Science And Technology, Seoul (KE)

( * ) Notice: Subject to any disclaimer, the term of this patent is extended or adjusted under 35 U.S.C. 154(b) by 184 days.

(21) Appl. No.: 14/072,308

(22) Filed: Nov. 5, 2013

(65) Prior Publication Data

US 2015/0094662 A1    Apr. 2, 2015

(30) Foreign Application Priority Data

Oct. 2, 2013 (KR) .................. 10-2013-0117763

(51) Int. Cl.
   *A61M 5/42* (2006.01)
(52) U.S. Cl.
   CPC .................................. *A61M 5/427* (2013.01)
(58) Field of Classification Search
   CPC .................................................. A61M 5/427
   See application file for complete search history.

(56) References Cited

U.S. PATENT DOCUMENTS

| | | | |
|---|---|---|---|
| 4,817,622 A * | 4/1989 | Pennypacker et al. | 600/473 |
| 6,923,762 B1 | 8/2005 | Creaghan, Jr. | |
| 7,841,751 B2 | 11/2010 | Mulani | |
| 7,874,698 B2 | 1/2011 | Mullani | |
| 7,983,738 B2 * | 7/2011 | Goldman et al. | 600/476 |
| 8,032,205 B2 | 10/2011 | Mullani | |
| 8,199,189 B2 | 6/2012 | Kagenow et al. | |
| 8,463,364 B2 * | 6/2013 | Wood et al. | 600/473 |
| 2008/0107309 A1 | 5/2008 | Cerni | |
| 2014/0121637 A1 * | 5/2014 | Boyden | A61B 19/201 604/506 |

FOREIGN PATENT DOCUMENTS

| | | | |
|---|---|---|---|
| KR | 10-2004-0095210 A | 11/2004 | |
| KR | 10-2010-0003478 A | 1/2010 | |
| KR | 10-2011-0092157 A | 8/2011 | |
| KR | 10-2012-0119523 A | 10/2012 | |
| KR | 10-2013-0028534 A | 3/2013 | |
| WO | WO 2013096850 A1 * | 6/2013 | ........... A61B 5/0059 |

OTHER PUBLICATIONS

V. P. Zharov et al., "Infrared Imaging of Subcutaneous Veins", 2004, Laser Surg. Med., vol. 34, pp. 56-61.
Y. L. Katsogridakis et al., "Veinlite transillumination in the pediatric emergency department: A therapeutic interventional trial", Pediatr. Emerg. Care., 2008, vol. 24, No. 2, pp. 83-88.

* cited by examiner

*Primary Examiner* — Ruth S Smith
(74) *Attorney, Agent, or Firm* — NSIP Law

(57) ABSTRACT

A visualization apparatus for the vein according to the present disclosure includes a near-infrared ray irradiating unit for irradiating near-infrared rays below the skin of a target area, an infrared camera unit for photographing the target area, an image processing unit for receiving and processing image information of a portion below the skin of the target area, photographed by the infrared camera unit, and providing the processed image information to a display device, and a display device located near the target area to display the image information provided from the image processing unit.

15 Claims, 5 Drawing Sheets

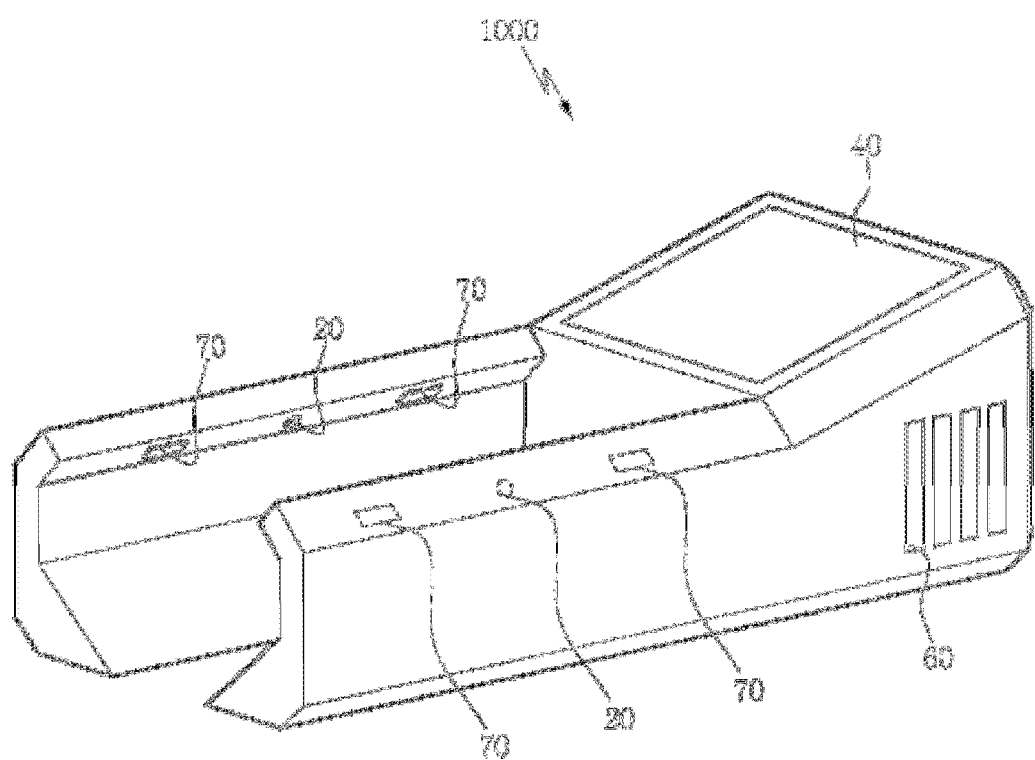

VISUALIZATION APPARATUS FOR VEIN

CROSS-REFERENCE TO RELATED APPLICATION

This application claims priority to Korean Patent Application No. 10-2013-0117763, filed on Oct. 2, 2013, and all the benefits accruing therefrom under 35 U.S.C. §119, the contents of which in its entirety are herein incorporated by reference.

BACKGROUND

1. Field

The present disclosure relates to a visualization apparatus for the vein, and more particularly, to a visualization apparatus for the vein, which may irradiate infrared rays and obtain and display an image so that a skin portion and the vein therein to which the venipuncture is performed may be observed simultaneously.

2. Description of the Related Art

The venipuncture means directly pricking the vein with an injection needle for intravenous injection, venous blood collection, venous pressure measurement or the like and is one of the most often used works. However, the accuracy of the venipuncture greatly depends on individual experiments and skills of an operator, and it is very difficult for skilled operators to perform the venipuncture to infants and children, obese patients, and patients with dark skin color.

According to related studies, the first-attempt success rate of the venipuncture is very low for such a patient group, which may cause bleeding, infection, displeasure or the like to the patients. For this reason, the venipuncture gives a large burden to not only patients but also operators. Many devices for visualizing the vein of a patient to assist the venipuncture have been proposed but not widely used due to low effect and high price.

Existing devices may be classified into a screen display type and a transillumination type depending on their operating methods, both of which have their own drawbacks and restrictions in use.

The screen display type device may use near-infrared rays having a wavelength range of 730 to 740 nm, which is most suitable for visualizing deoxygenated blood in the vein, but the screen hides the skin visually, which seriously deteriorates immediacy and accuracy.

Meanwhile, the transillumination type device reinforces the silhouette observed through the skin of a patient by projecting visible rays (red, orange, yellow or the like). In case of the transillumination type device, an operator may directly see the skin of a patent and the silhouette of the vein appearing through the skin without any obstacle, but should use visible rays instead of near-infrared rays, which inevitably deteriorates the quality of a vein image.

SUMMARY

The present disclosure is directed to providing a visualization apparatus, which may give a high-quality vein image while ensuring a visual field of an operator during the venipuncture.

In one aspect, there is provided a visualization apparatus for the vein, which includes: a near-infrared ray irradiating unit for irradiating near-infrared rays below the skin of a target area; an infrared camera unit for photographing the target area; an image processing unit for receiving and processing image information of a portion below the skin of the target area, photographed by the infrared camera unit, and providing the processed image information to a display device; and a display device located near the target area to display the image information provided from the image processing unit.

In addition, in the visualization apparatus for the vein, the near-infrared ray irradiating unit may have a predetermined inclination toward the target area so as to irradiate near-infrared rays to a portion below the skin of the target area through an outer skin of the target area.

In addition, in the visualization apparatus for the vein, the near-infrared ray may have a wavelength of 730 nm to 740 nm.

In addition, in the visualization apparatus for the vein, the wavelength of the near-infrared ray may be variable within a predetermined range.

In addition, in the visualization apparatus for the vein, the infrared camera unit may include at least one infrared camera for photographing the target area from different locations, and the display device may match images photographed by the at least one infrared camera and display a three-dimensional image for the portion below the skin of the target area.

In addition, the visualization apparatus for the vein may further include a laser irradiating unit for irradiating a visible ray guideline to the skin of the target area, and the display device may display a guideline corresponding to the irradiated visible ray guideline together with the image for the portion below the skin of the target area.

In addition, the visualization apparatus for the vein, the near-infrared ray irradiating unit, the infrared camera, the image processing unit and the display device may be embedded in a single hand-held device.

In addition, in the visualization apparatus for the vein, the near-infrared ray irradiating unit and the at least one infrared camera may be configured to surround the target area, and the near-infrared ray irradiating unit may be located to contact or be near the skin.

In addition, in the visualization apparatus for the vein, the image information may be an image for the vein below the skin of the target area.

In addition, in the visualization apparatus for the vein, the image processing unit may process the image information by means of an image optimizing algorithm using filtering, brightness/definition adjustment or the like and provide the image information to the display device.

In addition, in the visualization apparatus for the vein, the image processing unit may display the image information on the display device with the same magnification of an actual target area or in an enlarged or reduced size within a predetermined range.

In addition, the visualization apparatus for the vein may further include a cooling unit for discharging heat generated from the visualization apparatus for the vein.

According to the present disclosure, since an operator may not only watch a near-infrared ray vein image through a display device but also directly see the skin of a target area, the venipuncture may be performed more accurately and intuitionally, and this technique may be applied to various operations which need visual checking of the blood vessels in the skin.

BRIEF DESCRIPTION OF THE DRAWINGS

The above and other aspects, features and advantages of the disclosed exemplary embodiments will be more apparent from the following detailed description taken in conjunction with the accompanying drawings in which:

FIGS. 1a to 1c are perspective views showing a vein visualization apparatus 1000 according to an embodiment of the present disclosure;

DETAILED DESCRIPTION

Figure 1A:
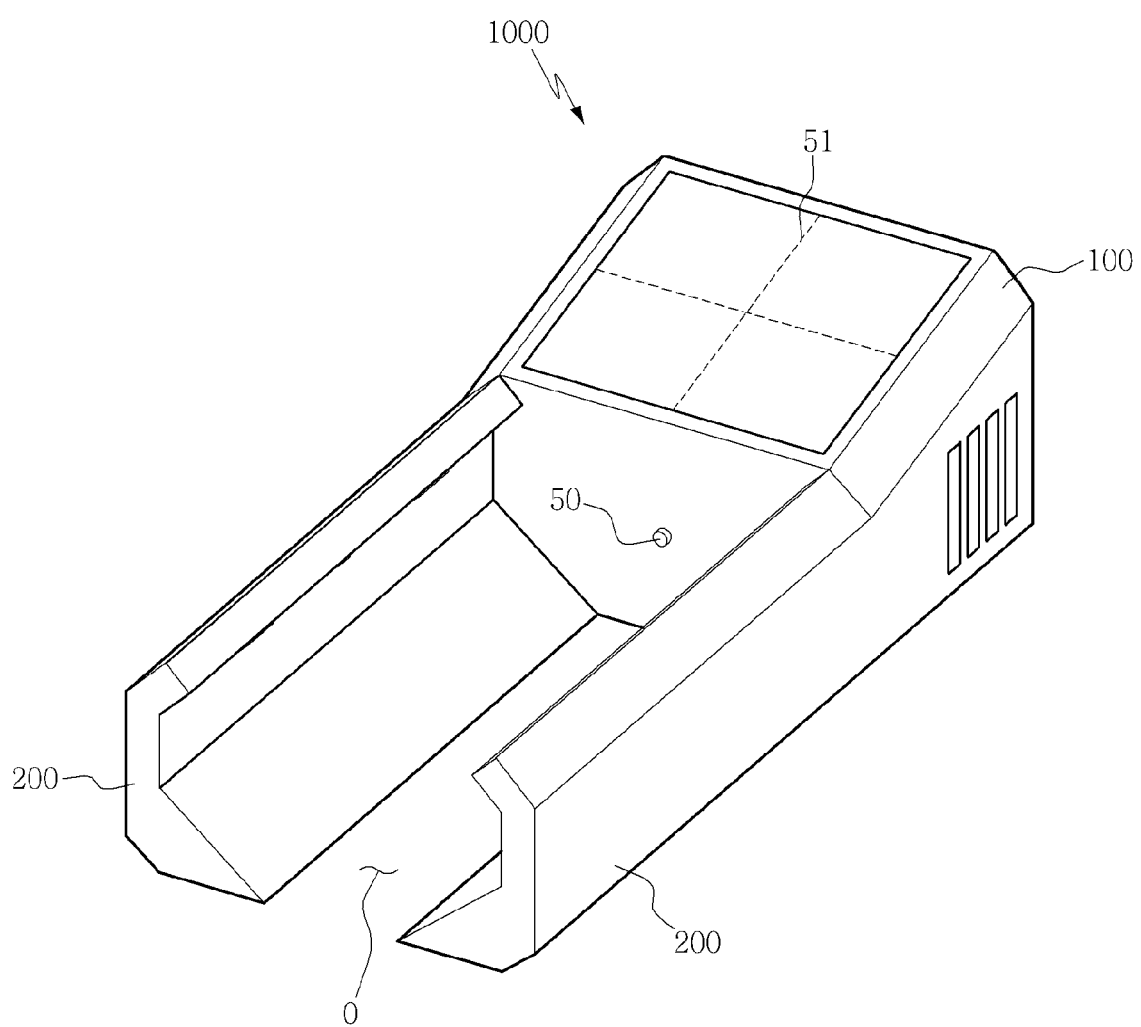

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. In the drawings, like reference numerals denote like elements. However, in the description, details of well-known features and techniques may be omitted to avoid unnecessarily obscuring the presented embodiments. In addition, the shape, size and regions, and the like, of the drawing may be exaggerated for clarity and may not mean the actual dimension.

Hereinafter, embodiments of the present disclosure will be described in detail with reference to the accompanying drawings.

Figure 1B:
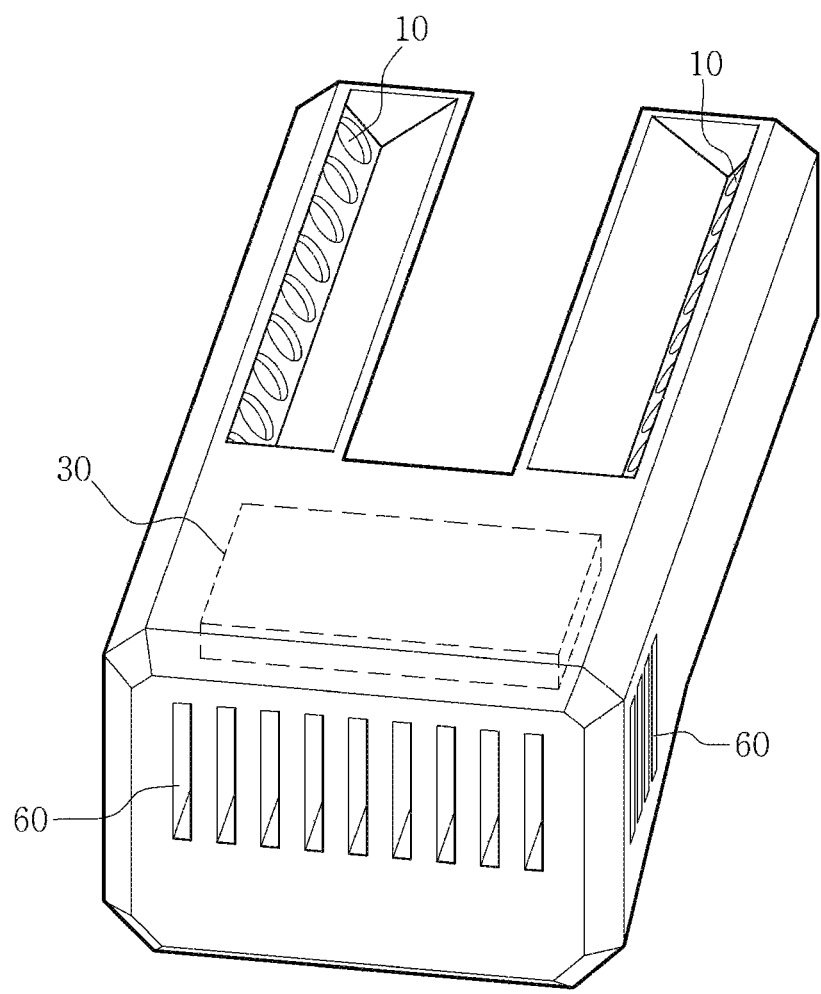

FIGS. 1a to 1c are perspective views showing a vein visualization apparatus 1000 according to an embodiment of the present disclosure. Referring to FIG. 1a, the vein visualization apparatus 1000 includes a main body 100 and an information detecting unit 200 surrounding a target area 0.

The main body 100 may include a power source (not shown) for operating the vein visualization apparatus 1000 and a control unit for processing various kinds of information. The control unit may include an image processing unit 30 or the like.

The target area 0 means a portion of the body which includes the vein to be visualized by an operator. The target area may be selected from various body portions such as arms, legs or the like, depending on the kind and purpose of diagnosis. The vein visualization apparatus 1000 according to an embodiment of the present disclosure is directed to photographing and displaying the vein in the skin of the target area 0.

The information detecting unit 200 allows an operator to visually watch the skin of the target area 0 and photographs a portion below the skin. For this, the information detecting unit 200 may not be located perpendicularly to the target area 0 but may be configured to surround the target area 0. Even though it is shown in FIGS. 1a to 1c that the information detecting unit 200 has a "⊂" shape and the target area has a rectangular shape, the information detecting unit 200 may also have another shape in another embodiment so that the target area has various shapes such as a circular shape or an oval shape. However, in this case, the information detecting unit 200 should not hide the target area so that the operator may perform the venipuncture while visually checking the skin (the surface) of the target area.

In an embodiment, the information detecting unit 200 may include a near-infrared ray irradiating unit 10 and at least one infrared camera 20. The near-infrared ray irradiating unit 10 irradiates near-infrared rays below the skin of the target area 0. The at least one infrared camera 20 photographs the target area 0.

Referring to FIG. 1b, the near-infrared ray irradiating units 10 are provided at both sides of the lower portion of the information detecting unit 200 to contact a periphery of the target area. As shown in FIG. 1b, in an embodiment, the near-infrared ray irradiating unit 10 may include a plurality of near-infrared ray lamps.

Referring to FIG. 1c, at least one infrared camera 20 is provided at both sides of the upper portion of the information detecting unit 200 to photograph the skin of the target area.

Figure 2:
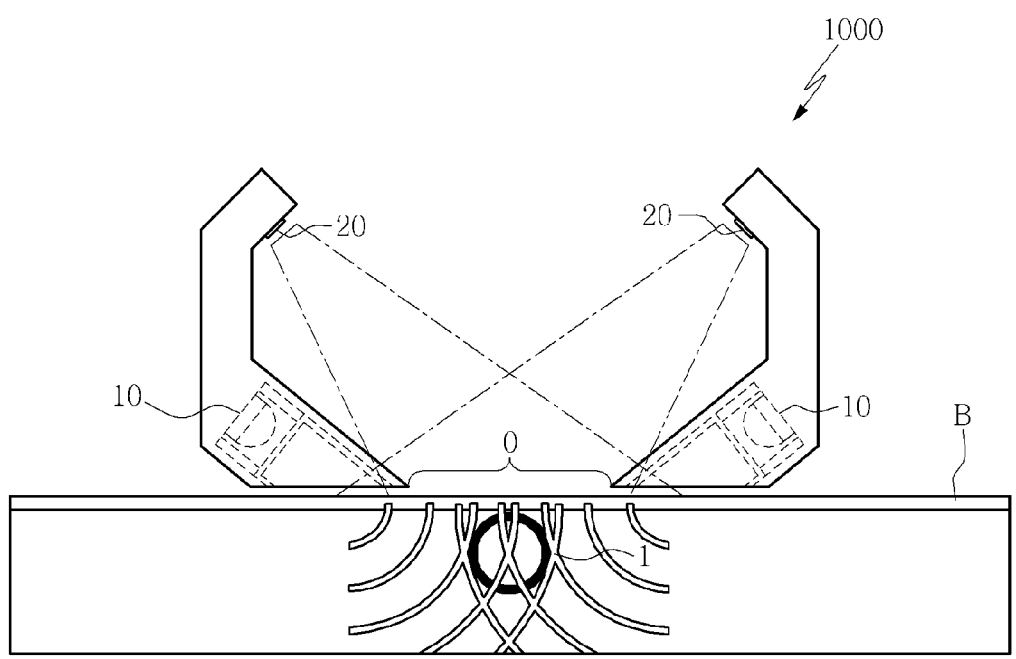
FIG. 2 is a diagram for illustrating functions and structures of a near-infrared ray irradiating unit 10 and an infrared camera 20 of the vein visualization apparatus 1000 according to an embodiment of the present disclosure.

FIG. 2 is a diagram for illustrating functions and structures of the near-infrared ray irradiating unit 10 and the infrared camera 20 of the vein visualization apparatus 1000 according to an embodiment of the present disclosure in more detail.

Referring to FIG. 2, the near-infrared ray irradiating unit 10 may irradiate near-infrared rays with a predetermined inclination toward the target area so that near-infrared rays are irradiated below the skin of the target area 0. Even though FIG. 2 shows that the lower portion of the information detecting unit 200 including the near-infrared ray irradiating unit 10 does not directly contact the skin B of a test subject, the lower portion of the information detecting unit 200 may also contact the skin B in another embodiment.

As shown in FIG. 2, since the near-infrared ray irradiating unit 10 irradiates near-infrared rays below the skin of the target area through the outer skin of the target area, the near-infrared rays are transferred into the skin B including the subcutaneous vein 1 or the like.

In an embodiment, the wavelength of the near-infrared ray irradiated by the near-infrared ray irradiating unit 10 may vary within a predetermined range. Accordingly, the body organs below the target area 0 may be observed suitable for the use.

In another embodiment, the near-infrared ray irradiated by the near-infrared ray irradiating unit 10 may have a wavelength of 730 nm to 740 nm. The near-infrared ray in the range of 730 nm to 740 nm has a higher deoxyhemoglobin absorbance than water and thus is most suitable for visualizing the venous blood in the vein. Therefore, any device for irradiating light to the target area 0 other than the near-infrared ray irradiating unit 10 is regarded as irradiating light having a wavelength out of the above range.

The infrared camera unit 20 may include at least one infrared camera which photographs the target area 0 at different locations. Referring to FIGS. 1c and 2, the infrared camera 20 is provided at the upper portion of the information detecting unit 200. The infrared camera 20 may be configured to be bent with a predetermined inclination toward the target area 0 so as to photograph the target area 0. Accordingly, as shown in FIG. 2, near-infrared rays may be transferred to the inside of the skin of the target area 0 by the near-infrared ray irradiating unit 10, and the skin of the target area 0 may be photographed by the infrared camera 20. The near-infrared ray irradiating unit and the infrared camera may be disposed at surfaces opposite to each other based on the target area 0.

The image processing unit 30 may receive image information about the portion below the skin of the target area 0 photographed by the infrared camera 20, process the received image information, and provide the processed image information to the display device 40.

In an embodiment, the image processing unit 30 may employ an image optimizing algorithm using filtering, brightness/definition adjustment or the like so that the subcutaneous vein 1 below the target area 0 may be shown more clearly.

In case of using at least two infrared cameras, the image processing unit 30 may match image information input by the at least two cameras and provide a single image to the display device 40. The matched image may be a two-dimensional image or a three-dimensional image. Accordingly, the two-dimensional image or the three-dimensional image for the subcutaneous vein below the target area 0 may be provided to the operator.

The display device 40 may receive and display the image information from the image processing unit 30. The display device 40 may be selected from various kinds of image display devices using LCD, LED, OLED, AMOLED or the like. In an embodiment, the display device may be located near the target area 0 as shown in FIGS. 1a to 1c. Accordingly, an operator may directly see the surface of the target area 0 and simultaneously watch the portion below the skin of the target area 0 through the display device 40. Since the target area and the display device are located in parallel, a sense of distance between both visual information (the surface of the target area and the inside of the vein), felt by the operator, may be reduced.

In another embodiment, the vein visualization apparatus 1000 may further include a laser irradiating unit 50 for irradiating a visible ray guideline to the skin of the target area 0. The laser irradiating unit 50 irradiates a guideline having a specific shape such as a + shape or a rectangular shape to the skin of the target area so that the operator may see the guideline. In this case, the display device 40 may display a guideline corresponding to the irradiated visible ray guideline together with the image of the portion below the skin of the target area. In detail, the image of the portion below the skin of the target area may be displayed to be overlapped with a specific guideline.

Figure 3:
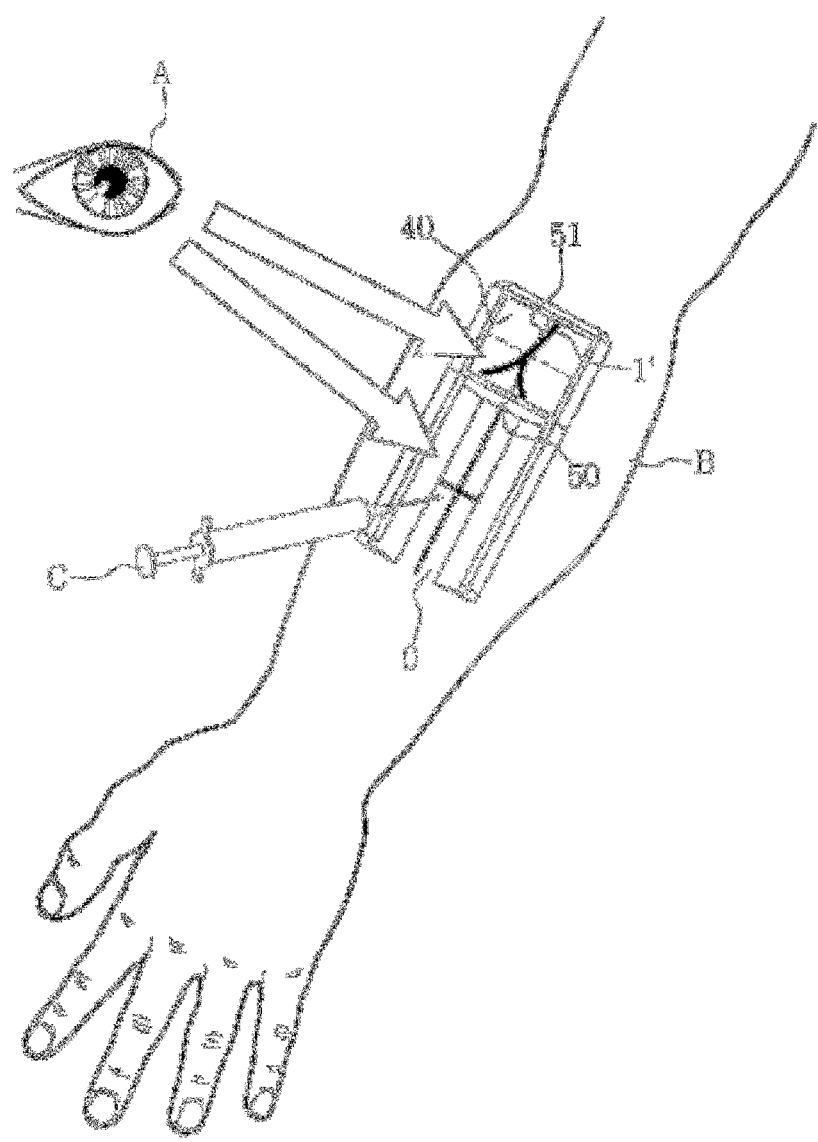
FIG. 3 is a diagram for illustrating a use of the vein visualization apparatus according to an embodiment of the present disclosure.

FIG. 3 is a diagram for illustrating a use of the vein visualization apparatus according to an embodiment of the present disclosure. Referring to FIG. 3, the visible ray guideline irradiated by the laser irradiating unit 50 and a guideline 51 corresponding to the visible ray guideline are displayed by the display device.

For example, the image displayed by the display device 40 may have the same magnification as the portion below the skin of the actual target area, and the operator may perform the venipuncture with reference to both guidelines. Accordingly, the accuracy of the venipuncture may be improved. In addition, in another embodiment, the magnification may vary, which allows displaying a greater or smaller image than the size of the vein below the actual target area.

In another embodiment, the information detecting unit 200 may further include a visible ray emitting unit 70. As shown in FIG. 1c, the visible ray emitting unit 70 may be disposed in parallel to the near-infrared camera 20. The visible ray emitting unit 70 emits light to the surface of the target area and helps the operator to easily observe the skin of the target area by naked eyes.

In an embodiment, as shown in FIGS. 1a to 1c, the vein visualization apparatus 1000 may be a single handheld device including the near-infrared ray irradiating unit 10, the infrared camera 20, the image processing unit 30 and the display device 40. For example, all components may be housed in a single device and carried together.

In another embodiment, the vein visualization apparatus 1000 may further include a cooling unit 60 for discharging heat generated from each component. The cooling unit may include a fan to discharge heat to the outside.

Referring to FIG. 3, the visual field A of the operator may check the images for the surface of the target area and the vein below the target area simultaneously by using the vein visualization apparatus 1000 described above (for example, these images may be implemented as a three-dimensional image).

Even though the visualization apparatus for the vein according to an embodiment of the present disclosure is used for performing the venipuncture, it should be understood that the visualization apparatus may also be utilized in various medical fields such as varicose vein treatment, which require visualization of the vein.

Though the present disclosure has been described with reference to the embodiments depicted in the drawings, it is just an example, and it should be understood by those skilled in the art that various modifications and equivalents can be made from the disclosure. However, such modifications should be regarded as being within the scope of the present disclosure. Therefore, the true scope of the present disclosure should be defined by the appended claims.

What is claimed is:

1. An apparatus for visualization of a blood vessel of a subject, comprising:
   first and second infrared cameras configured to image a target area in infrared spectrum;
   an image processor configured to receive and process image information of a portion below a skin of the target area, imaged by the first and second infrared cameras;
   a display positioned on a main body and configured to receive the processed image information from the image processor;
   first and second parallel arms extending from the main body;
   a first irradiation array positioned on the first arm; and
   a second irradiation array positioned on the second arm,
   wherein the first infrared camera is positioned on the first arm, and the second infrared camera is positioned on the second arm, and
   wherein the first and second irradiation arrays are configured to irradiate the portion with near-infrared rays.

2. The apparatus according to claim 1,
   wherein the first arm comprises a first inclination and the second arm comprises a second inclination such that the first and second irradiation arrays are configured to irradiate near-infrared rays to the portion below the skin of the target area through an outer skin of the target area.

3. The apparatus according to claim 1,
   wherein first and second irradiation arrays are configured to provide near-infrared rays having a wavelength between 730 nm and 740 nm.

4. The apparatus according to claim 1,
wherein the first and second irradiation arrays are configured to provide near-infrared rays having a wavelength variable within a range.

5. The apparatus according to claim 1,
wherein the display is configured to match images from the first and second infrared cameras and display a three-dimensional image for the portion below the skin of the target area.

6. The apparatus according to claim 1, further comprising a laser irradiator configured to provide a visible ray guideline onto the skin of the target area,
wherein the display is further configured to display a virtual guideline corresponding to the visible ray guideline together with the image for the portion below the skin of the target area.

7. The apparatus according to claim 1,
wherein the image processor is further configured to process the image information using an image optimizing algorithm, and provide the processed image information to the display.

8. The apparatus according to claim 1,
wherein the image processor is further configured to display the image information on the display without any magnification of the target area, or in an enlarged or reduced size within a range.

9. The apparatus according to claim 1, further comprising a cooler configured to discharge heat generated from the apparatus.

10. The apparatus according to claim 1, wherein the first infrared camera is located at a first end of the first arm and the second infrared camera is located at a first end of the second arm.

11. The apparatus of claim 10, wherein the first irradiation array is positioned at a second end of the first arm, the second irradiation array is positioned at a second end of the second arm, the first end of the first arm is opposite to the second end of the first arm, and the first end of the second arm is opposite to the second end of the second arm.

12. The apparatus of claim 1, wherein:
the first arm comprises a first inclined surface forming an acute angle with a lower surface of the first arm, a first vertical portion extending from the first inclined surface and being perpendicular to the lower surface of the first arm, and a first angled portion forming an obtuse angle the first vertical portion, and
the second arm comprises a second inclined surface forming an acute angle with a lower surface of the second arm, a second vertical portion extending from the second inclined surface and being perpendicular to the lower surface of the second arm, and a second angled portion forming an obtuse angle the second vertical portion.

13. The apparatus of claim 12, wherein the main body comprises a laser configured to project a light pattern onto the target area.

14. The apparatus of claim 13, wherein the first angled portion comprises a first visible light emitter configured to project visible light onto the target area, the second angled portion comprises a second visible light emitter configured to project visible light onto the target area, the first infrared camera is positioned on the first angled portion, and the second infrared camera is positioned on the second angled portion.

15. The apparatus of claim 12, wherein the first and second angled portions extend towards each other.

* * * * *